(12) United States Patent
Hoadley et al.

(10) Patent No.: US 9,386,912 B2
(45) Date of Patent: *Jul. 12, 2016

(54) APPARATUS AND METHOD FOR LIGHTING A SURGICAL FIELD

(71) Applicant: VIKON SURGICAL, LLC, Birmingham, AL (US)

(72) Inventors: Bruce Hoadley, Birmingham, AL (US); Lucus Parker Cohn, Moody, AL (US); Austin Crowder, Dallas, TX (US)

(73) Assignee: VIKON SURGICAL, LLC, Birmingham, AL (US)

( * ) Notice: Subject to any disclaimer, the term of this patent is extended or adjusted under 35 U.S.C. 154(b) by 95 days.

This patent is subject to a terminal disclaimer.

(21) Appl. No.: 14/220,856

(22) Filed: Mar. 20, 2014

(65) Prior Publication Data

US 2014/0275789 A1      Sep. 18, 2014

Related U.S. Application Data

(63) Continuation-in-part of application No. 11/259,978, filed on Oct. 27, 2005, now Pat. No. 8,789,962.

(51) Int. Cl.
| | |
|---|---|
| *A61B 1/06* | (2006.01) |
| *F21V 21/084* | (2006.01) |
| *F21V 8/00* | (2006.01) |
| *F21Y 101/02* | (2006.01) |
| *F21Y 113/00* | (2016.01) |
| *F21V 29/70* | (2015.01) |

(52) U.S. Cl.
CPC ............. *A61B 1/0638* (2013.01); *A61B 90/36* (2016.02); *F21V 21/084* (2013.01); *G02B 6/0006* (2013.01); *A61B 2090/502* (2016.02); *F21V 29/70* (2015.01); *F21Y 2101/02* (2013.01); *F21Y 2113/005* (2013.01); *Y10S 362/804* (2013.01)

(58) Field of Classification Search
CPC .. A61B 1/0661; A61B 1/0684; A61B 1/0676; A61B 10/0692; A61B 1/0669; A61B 90/36; A61B 1/0638; G02B 6/0006
See application file for complete search history.

(56) References Cited

U.S. PATENT DOCUMENTS 5,056,881 A * 10/1991 Bowen .................. G02B 6/4208
359/19
5,634,711 A * 6/1997 Kennedy .............. A61C 19/004
315/224

FOREIGN PATENT DOCUMENTS

EP        0381883 A1 *   8/1990   .......... A61B 5/14553

* cited by examiner

*Primary Examiner* — Robert May
(74) *Attorney, Agent, or Firm* — C. Brandon Browning; Maynard, Cooper & Gale, PC

(57) ABSTRACT

A surgical light that uses multiple LEDs to produce superior illumination. Heat sinks are used to help dissipate heat produced from the LEDs. The light from the LEDs is directed, using collimizers, into fiber optic cables. The fiber light from the optic cables, using an LED combiner, is then combined and focused on a working area. The LED combiner may include an adjustable lens so that the device's illumination may be focused at multiple focal distances and with varied areas of illumination. The LEDs may be powered by a battery and may comprise one or more red LEDs, one or more blue LEDs, and one or more green LEDs. The surgical light may be used configured for use with headlamps, surgical scopes and the like.

15 Claims, 5 Drawing Sheets

APPARATUS AND METHOD FOR LIGHTING A SURGICAL FIELD

RELATED APPLICATIONS

This application is a continuation-in-part and claims priority to U.S. Non-Provisional patent application Ser. No. 11/259,978, filed on Oct. 27, 2005, and titled, "Surgical Headlight," the entire contents of which are incorporated herein by reference.

FIELD OF THE INVENTION

The present invention relates to apparatuses and methods for illuminating work areas such as surgical fields. More particularly, the present invention is directed to a surgical light including a plurality of light sources light sources selectively actuated to emit light and a combiner including a scrambler in optical communication with the light sources to receive the light emitted from the light sources and output substantially-uniform combined light with substantially-uniform intensity and color distribution.

BACKGROUND OF THE INVENTION

Medical providers use surgical headlights to illuminate a surgical field. Such headlights are worn on the medical provider's head and may utilize halogen or metal halide light sources, as well as xenon lights, to provide illumination. The Xenon light source may be located on a rack. The light source projects light, via a fiber optic cable, to the headlight system. Light emitting diodes (LEDs) may also be used, providing various advantages over prior illumination methods including reducing the weight, cost, heat, maintenance and discomfort generally associated with the traditional headlight. Drawbacks for these devices include: limited bulb life, excessive cost, fragile fiber optic cables, insufficient illumination, and limited mobility for the user.

Examples of related devices include the 49820 Xenon Surgical Headlight System from WelchAllyn [WelchAllyn, Inc., 4341 State Street Road, Skaneateles Falls, N.Y. 13153-0220 USA]. The device connects a Xenon light source, instead of LEDs, to a headlamp using fiber optic cables. The device is attached to a light source that has limited to no mobility. This constrains the user who is tethered, via the fiber optic cable, to the light source. Unsurprisingly, the fiber optic connection between the lamp and light source is placed under great strain, resulting in reliability issues for the headlight unit. WelchAllyn also supplies the 49020 5 watt LED Procedure Headlight, which utilizes a single 5 watt LED and produces 100 Lumens of white light. In addition, the HALO headlight, by Enova Medical Technologies [1839 Buerkle Road, St. Paul, Minn. 55110 USA], uses two white LEDs and no fiber optic cables. However, the prior art's limited use of LEDs results in brightness that is not optimal, thereby producing less light than more traditional surgical headlights such as Xenon-board devices.

Thus, a need exists for a mobile surgical headlight that utilizes LEDs to lower cost, weight and heat, while still providing light adequate to illuminate the working area.

SUMMARY OF THE INVENTION

In one embodiment of the invention, a surgical headlight comprises multiple LEDs. Each LED is powered by a battery. Each LED is coupled to a heat sink to promote heat dissipation. Furthermore, each LED is connected to a collimator that directs light from the LED into a fiber optic cable. The collimator may comprise or be coupled to one or more lenses. The fiber optic cables guide light from the LED towards a LED combiner. There, the light from each LED is directed so that each LED's light is combined with light from the other LEDs. The surgical headlight produces light having an intensity that is greater than about 100 lumens. In other embodiments of the invention, the headlight produces light having an intensity that is greater than about 300 lumens. Still other embodiments produce light greater than about 500 lumens.

In another embodiment of the invention, the headlight comprises three

LEDs while in other embodiments, the headlight comprises six, nine or twelve LEDs. In one embodiment of the invention, a blue LED, a red LED and a green LED combine to produce white light. In another embodiment, a filter is used to remove color components from one or more LEDs. In still another embodiment, current balancing circuitry is used to vary the intensity of one or more of the multiple LEDs.

In yet another embodiment of the invention, the LED combiner comprises a lens and an actuator for actuating the lens. As a result, the light from the LEDs may be focused at various focal points.

In still another embodiment of the invention, the collimator comprises a dowel.

In another embodiment of the invention, the LEDs are mounted on a headlight. In other embodiments, the LEDs are mounted on a belt worn around the user's waist or on a belt fastened to the user's arm. The battery or batteries, that supply energy to LEDs, may be mounted on the headlight or on a belt worn around the user's waist or arm.

One embodiment of the invention weighs less than about 12 ounces.

In still another embodiment, the invention is used to illuminate a surgical scope or, for example, a retractor involved in endoscopic procedures. In this embodiment, the invention includes a housing containing at least two light sources selectively actuated to emit light, at least one heat sink in thermal communication with the two light sources to receive thermal energy from the light sources and dissipate the thermal energy received, and a combiner. The combiner includes a scrambler in optical communication with the two light sources to receive the light emitted from the light sources and output substantially-uniform combined light with substantially-uniform intensity and color distribution. A collimator may be coupled to each of the two light sources for directing light to the combiner.

A light transmission member, such as a glass or plastic fiber optical cable, operatively couples to the combiner for receiving and transmitting the substantially-uniform combined light. The light transmission member includes a distal tip having a coupler configured for operatively coupling the light transmission member to a surgical device such as an endoscope. The coupler may be any coupler known in the art for optically linking light source to a surgical scope.

The foregoing has outlined rather broadly the features of the present invention in order that the detailed description of the invention that follows may be better understood. Additional features and advantages of the invention will be described hereinafter, which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DESCRIPTION OF THE PREFERRED EMBODIMENTS

Figure 1:
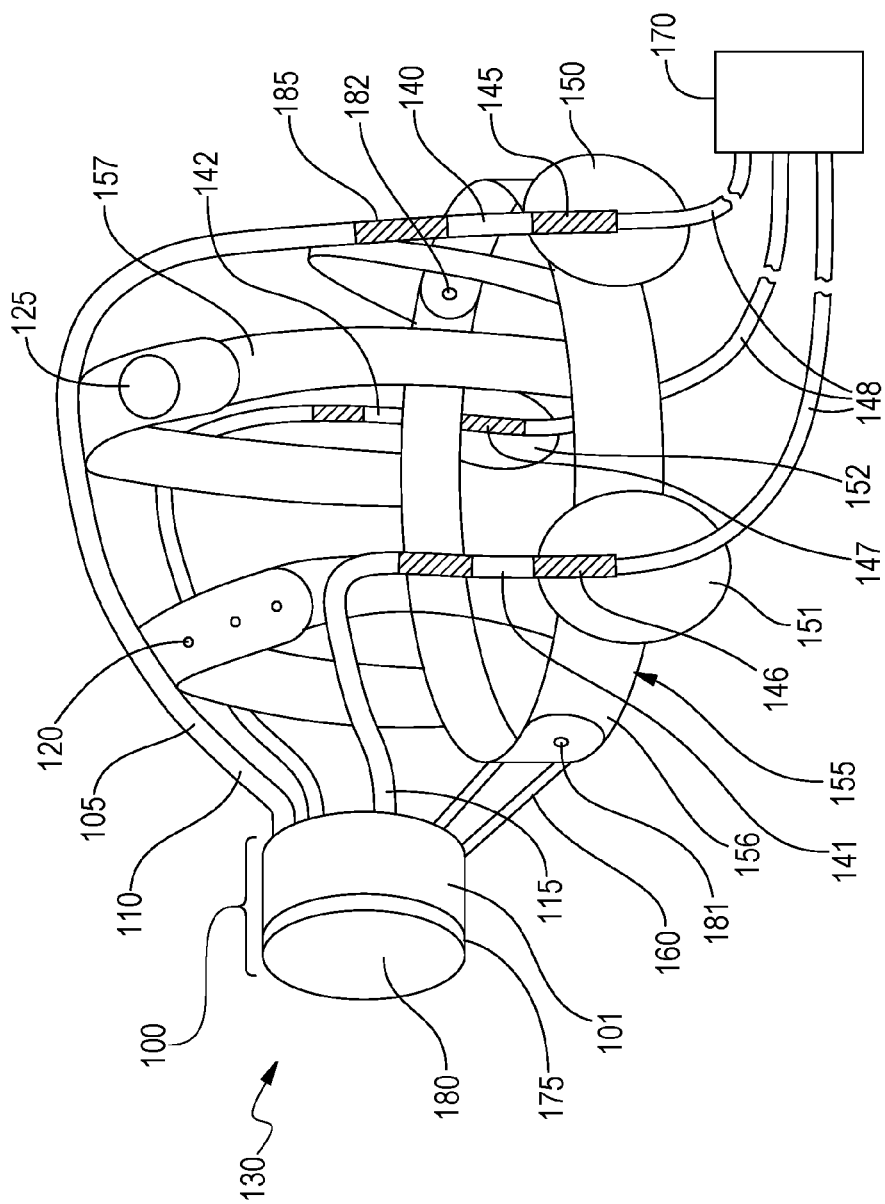
FIG. 1 is an example of one embodiment of a surgical headlamp.

FIG. 1 illustrates one embodiment of the invention. A surgical headlight 130 comprises three LEDs 145, 146, 147. Each LED 145, 146, 147 is powered by a battery 170. Each LED 145, 146, 147 may be powered by its own power supply (e.g., battery 170) or one power supply may power all of the LEDs 145, 146, 147. The LEDs 145, 146, 147 may connect to the battery 170 (e.g., lithium-ion) via electrically shielded cables 148 or, for example, an integrated circuit or BUS. The battery may be located on a headlight 130 or on a belt fastened to the user's arm or waist. In one embodiment of the invention, the battery 170 is capable of producing 10 volts per every 5 watt LED and could last 4 or more hours between recharging sessions. The battery 170 may be capable of "hot swapping" whereby a charge is retained thereby allowing the headlamp 130 to temporarily produce light while batteries 170 are exchanged.

Each LED 145, 146, 147 may be coupled to a heat sink 150, 151, 152 to promote heat dissipation. Each LED may be coupled to its own individual heat sink 150 or multiple LEDs 145, 146, 147 may utilize one such heat sink. In addition, fans may be used to cool the LEDs 145, 146, 147 and/or heat sink 150. Heat sinks 150, 151, 152 are provided because high powered LEDs 145, 146, 147 produce heat that must be dissipated to avoid causing the user discomfort. Due to the amount of heat generated by the LEDs 145, 146, 147, the heat sinks 150, 151, 152 may be distanced from the user by one to two inches. Such a position not only allows the user to be located a reasonable distance from the heat source, but also allows for airflow around the LED to promote cooling. The heat sinks 150, 151, 152 may have a "waffle" or "honeycomb" shape to increase their surface area and thus enable faster dissipation of heat. The heat sinks may be made of any low weight, conductive material such as, for example, airplane aluminum, polycarbonate/metal alloys, fiber glass or bubble glass.

The LEDs 145, 146, 147 selected may, for example, comprise the 5 watt Luxeon III Star and/or Luxeon V Star, available from Lumileds Lighting, LLC (370 West Trimble Road, San Jose, Calif., 95131 USA). Those of ordinary skill in the art will appreciate that other LEDs may be used. Lower wattage LEDs (e.g., 1 or 3 watts) may also be used if less heat and brightness are acceptable design choices. The LEDs may be selected according to the desired end use for the headlamp 130. For example, in neurological surgery, tissue differentiation is critical and thus, white light, of extreme brightness, is advantageous. Furthermore, "cool" lighting is desirable in order to avoid drying tissues during a procedure. To that end, color temperature of 5,000 degrees Kelvin, or less, may be advantageous.

To achieve a high level of bright white light (e.g., 500 lumens) with LEDs, blue LEDs may be filtered, thus leaving white light. In addition, such light may be generated by using a combination of lights such as, for example, red, blue, and green lights. In one embodiment of the invention, as seen in FIG. 1, the headlight 130 is composed of three LEDs 145, 146, 147 including one red 145, one green 146 and one blue 147 LED. To increase brightness, other embodiments of the invention may comprise six, nine or twelve LEDs. For example, one embodiment of the headlight 130 may comprise four red LEDs, four green LEDs and four blue LEDs. According to design preference, a red LED 145 may, for example, be replaced or coupled with a red-orange or amber LED. A blue LED 147 may be replaced or coupled with royal blue LEDs. Choosing different colors, and possibly adjusting current delivered to such LEDs, allows the headlight 130 to achieve varied levels of brightness in exchange for, as an example, varied levels of power consumption. Such flexibility also allows for cost, performance, and availability variances associated with differently colored LEDs to be accounted for without substantially varying the operation principles of the headlight 130.

In one embodiment, color LEDs may be coated with a phosphorus coating to create white light from, for example, a blue LED 147. As those of ordinary skill in the art will appreciate, color LEDs or LEDs with varied coatings may be incorporated into the headlight 130 to compensate for light color that is missing from the headlight 130 light spectrum.

To vary the intensity of light produced from each LED 145, 146, 147, a person of ordinary skill in the art will appreciate how current balancing circuitry may be used to distribute current in varying levels to different LEDs. Accordingly, less current may be supplied to, for example, the red LED 145 than the blue LED 147. Adjusting the current level allows the headlamp 130 to produce white light with no color tint. However, high current levels may be supplied to, for example, the red LED 145 to produce light with a red tint. Different medical users may choose different tints to illuminate varied tissues such as, blood vessels, bone or connective tissue. As appreciated by those of skill in the art, various techniques for dimming light from all or any LED 145, 146, 147 may be used. Typical techniques include pulse width modulation or current amplitude dimming with, for example, potentiometers and related circuitry. In one embodiment, an Ostar, available from Osram Semiconductors (Gmbh Wernerwerkstrasse 2 D-93049, Regensburg, Germany) (www.osram-os.com), may be used to adjust illumination from different colored LEDs to produce white light.

Referring to FIG. 1, the LEDs 145, 146, 147 may be coupled to an LED driver to regulate current to the LEDs. An example of such a driver is the 12VDC 5W LED Drive Module PowerPuck (Model # 2008) from LED dynamics. (LuxDrive, Division of LEDdynamics, Inc., 44 Hull Street, Randolph, Vermont 05060-0444). Such a DC to DC converter delivers a fixed output current by varying the output voltage as required to maintain the specified current. The drivers may be calibrated so that different levels of current are supplied to different LEDs to ensure white light is produced. Such current levels may be fixed or variable, as appreciated by those of ordinary skill in the art.

Through use of multiple LEDs, the surgical headlight 130 may produce light having an intensity greater than about 300 lumens. Blue LEDs are typically capable of 23 lumens, red LEDs may produce 140 lumens and green LEDs may produce 64 lumens. When white light of insufficient brightness is produced, the number of LEDs can be increased. Using, for example, twelve LEDs may produce light having an intensity that is greater than about 500 lumens.

Figure 2:
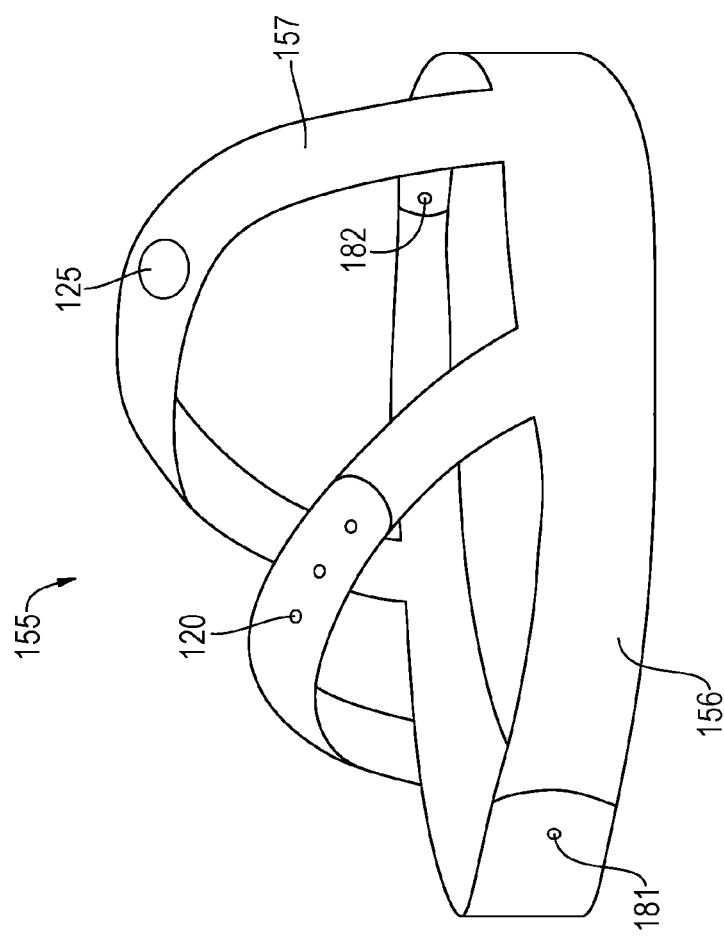
FIG. 2 is an example of one embodiment of headset for use with a surgical headlamp.

The LEDs 145, 146, 147 may attach, directly or indirectly, to a headset 155. (See also FIG. 2). As shown in FIG. 1, the headset 155 may incorporate one or more ratchets 125 to allow for adjustments so the apparatus may accommodate multiple users. The ratchets 125 may be located on the horizontal band 156 and a vertical band 157. Separate bands may be used whereby, through use of various holes 120 and probes, the headset 155 may be customized further. The headset 155 may be composed of semi-ridged plastic. The headset 155 may be constructed so that it is rigid enough to uphold the weight of the LEDs 145, 146, 147 and heat sinks 150, 151 and 152. In addition, the headset 155 may comprise hinges or pivots 181, 182 located on the horizontal band 156, thereby allowing the headlight 130 to collapse into a compact form provided, for example, the vertical bands 157 can be unattached from the headset 155. In other embodiments, instead of attaching to a headset 155, the LEDs 145, 146, 147 are mounted on a belt worn around the user's waist or on a belt fastened to the user's arm.

Furthermore, each LED 145, 146, 147 may be connected to a collimator 140, 141, 142 that directs light from the LED 145, 146, 147 into a fiber optic cable 105, 110, 115. The fiber optic cables 105, 110, 115 guide light from each LED 145, 146, 147 towards a LED combiner 100. The fiber optic cables 105, 110, 115 may extend, independently, from the LEDs 145, 146, 147 to the LED combiner 100. However, they may also be bundled together, in a shielded shroud, to further protect the fiber optic cables 105, 110, 115.

In one embodiment of the invention, a collimator 140, 141, 142 may be avoided by directly connecting the LED 145, 146, 147 to the fiber optic cable 105, 110, 115. In other embodiments, however, a collimator 140, 141, 142, such as the LAHL-NX05 Luxeon Collimator, may be used. (Lumileds Lighting, LLC, 370 West Trimble Road, San Jose, Calif., 95131). Collimators with, for example, 90% efficiency may allow for the use of fewer LEDs to obtain the desired level of brightness. As understood by a person or ordinary skill in the art, items such as glass dowels may be used instead of or in addition to a collimator 140, 141, 142.

In the LED combiner 100, the light from each LED 145, 146, 147 is directed so that each LED's light is combined with light from the other LEDs. The light from each LED 145, 146, 147 may be combined at the LED combiner 100 or projected on a path such that the light from each LED 145, 146, 147 is combined at a focal point that is, for example, twenty-four inches away from the headlight 130. The LED combiner 100 may comprise or be coupled to a fiber optic cable coupler, such as, for example, the 3 to 1 coupler from FOCI Fiber Optic Communications, Inc. (20550 Nordhoff St., Chatsworth, Calif. 91311 USA). In one embodiment, the LED combiner 100 may utilize a RGB scrambler 101 to combine the red, green and blue light into, for example, white light. As those or ordinary skill in the art will appreciate, an RGB scrambler 101 or combiner 100, comprised of, for example, multi-gradient lenses may be used. The LED combiner 100 may further comprise a lens 180 and an actuator 175 for actuating the lens. As a result, the light from the LEDs 145, 146, 147 may be focused at various focal points. For example, the light may be focused at 18 inches, 30 inches, or at any point therebetween, to accommodate a user's preferences. The LED combiner 100 may be supported using brackets 160 and/or a telescoping mount. Furthermore, the lens 180 may also cooperate with a pivot joint to allow the user to direct the light beam.

Figure 3:
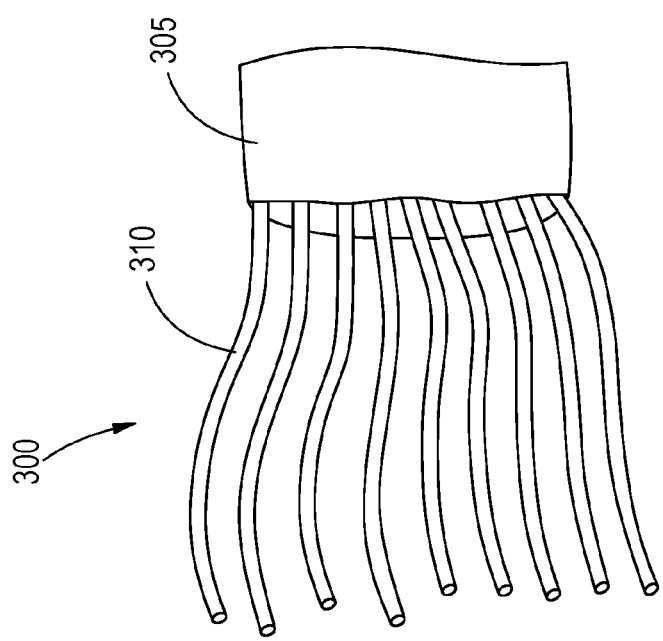
FIG. 3 is an example of one embodiment of a LED combiner.

As shown in FIG. 3, The LED combiner 300 may be constructed by molding, fiber splitting or by gluing glass/quartz single fibers to a base 305 that comprises a lens. Acrylic, polycarbonate, high clarity plastic or any other molded material with low light resistance may be used in constructing the LED combiner 300. Flexible glass or quartz fiber reinforced with a thin coating, for protection, may also be used. A transparent adhesive may be used to couple the fiber optic cable 310 to the LED combiner base 305. The base 305 could be manufactured as a separate piece from the cables 310.

Multiple glass fibers could be used with the headlamp 130. For example, a fiber bundle (e.g., 5,000 to 10,000 fibers) could be split and run to each individual collimator 140, 141, and 142.

Those of ordinary skill in the art will appreciate that a laser may substitute for the LEDs 145, 146, 147. For example, white lasers may be so utilized. The LEDs 145, 146, 147 may be coupled to a fiber optic cable 105, 110, 115. However, the laser may be affixed to, for example, the headlight 130 and project light onto the surgical field without use of any fiber optic cable.

One embodiment of the invention weighs less than about 12 ounces.

Figure 4:
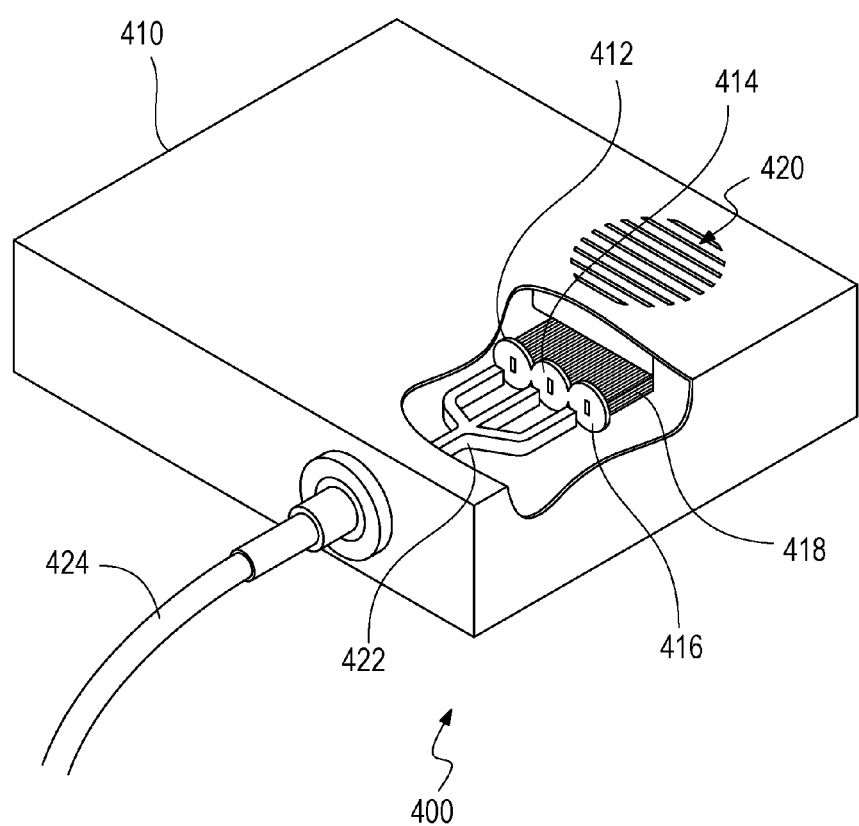
FIG. 4 is a perspective view of an LED powered light source in accordance with the present invention mounted in a mechanical box.
Figure 5:
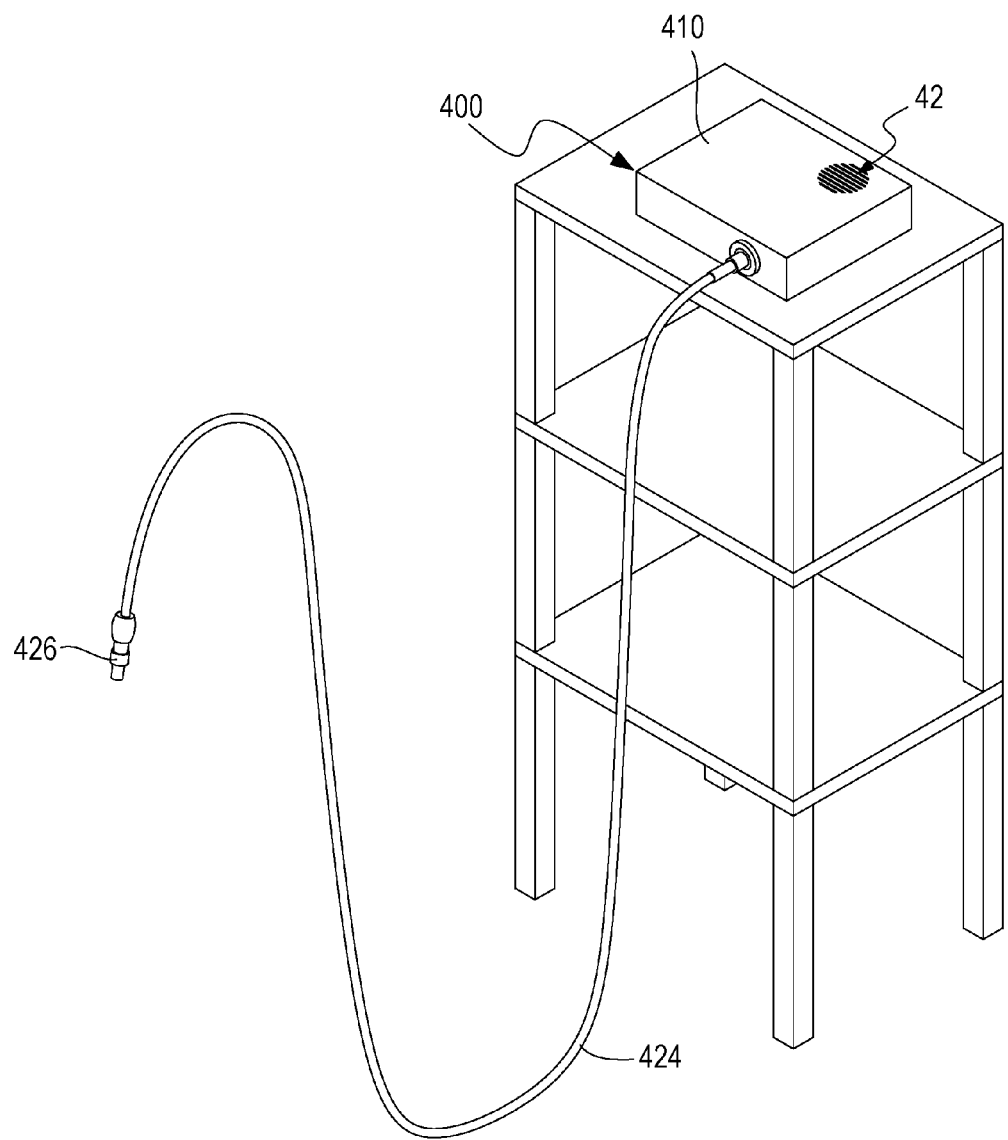
FIG. 5 is a perspective view of the LED powered light source of FIG. 3 configured for transmitting light to an endoscope.

In still another embodiment, the invention is used to illuminate a surgical scope involved in endoscopic procedures such as, for example, laparoscopic gall bladder removal. Illustrated in FIG. 4 is an example of one embodiment of an LED powered light source 400, in accordance with the present invention, mounted in a mechanical box 410 and configured for transmitting light to a surgical scope (not shown), such as an endoscope. Surgical illumination light source 400 includes three LED's 412, 414 and 416 mounted on a heat sink 418 in mechanical box 410 housing and a cooling fan 420. LED 412 emits red light, LED 414 emits blue light and LED 416 emits green light. LED's 412, 414 and 416 may be powered from a single power supply (e.g. battery or A/C power supply) and/or each LED 412, 414 or 416 may be powered from a distinct power supply incorporated within the light source box 410. Power may also be delivered from an array of multiple power supplies whose power output is transformed and modulated by circuitry and/or software which has been preprogrammed, including a predetermined set of parameter(s) and/or whose parameter(s) may be adjusted by the user via an interface on mechanical box 410 which controls LED's 412, 414 and 416 to achieve the desired light quality. The light source 400 delivers light to an LED collimator-combiner 422 which then delivers light to an optical fiber 424. Optical fiber 424 terminates in a coupler 426 which is configured for operatively coupling the optical fiber to a light projection module of the endoscope for delivering light to optical fibers within the endoscope which, in turn, emit light onto the working area of the surgical field.

As will be apparent to one skilled in the art, various modifications can be made within the scope of the aforesaid description. Such modifications being within the ability of one skilled in the art form a part of the present invention and are embraced by the claims below. For example, the headlight 130 is also appropriate for other lighting environments including: dental, emergency room, paramedics, auto mechanics and mineral mining.

The presently disclosed embodiments are to be considered in all respects as illustrative and not restrictive. The scope of the invention is indicated by the appended claims, rather than the foregoing description, and all changes which come within the meaning and range of equivalency of the claims are, therefore, intended to be embraced therein.

What is claimed is:

1. An apparatus for illuminating a surgical field comprising:

at least two light sources selectively actuated to emit light, at least one heat sink in thermal communication with at least one of the two light sources to receive thermal energy from the at least one of the two light sources and dissipate at least a portion of the thermal energy received, a combiner including a scrambler in optical communication with the at least two light sources to receive at least a portion of the light emitted from each of the light sources and output substantially-uniform combined light with substantially-uniform intensity and color distribution, and a light transmission member operatively coupled to the combiner for receiving and transmitting the substantially-uniform combined light, the light transmission member including a distal tip having a coupler configured for operatively coupling the light transmission member to an endoscope.

2. The apparatus according to claim 1 further comprising a housing in which the at least two light sources and the combiner are at least partially contained.

3. The apparatus according to claim 2 wherein the housing contains the at least one heat sink and a fan.

4. The apparatus according to claim 1 wherein the at least two light sources includes a red LED, a blue LED and a green LED.

5. The apparatus according to claim 1 wherein the light transmission member includes plastic optical fibers.

6. The apparatus according to claim 1 further comprising a collimator operatively coupled to each of the at least two light sources for directing light to the combiner.

7. A method of illuminating a surgical field comprising providing the apparatus of claim 1 and directing light created by the at least two light sources through the endoscope into the surgical field.

8. A surgical-illumination system comprising:
at least two light sources selectively actuated to emit light,
a combiner including a scrambler in optical communication with the at least two light sources to receive at least a portion of the light emitted from the at least two light sources and output substantially-uniform combined light with substantially-uniform intensity and color distribution, and
an endoscope operatively coupled to the at least two light sources.

9. The system according to claim 8 further comprising a light transmission cable operatively coupled to and between the at least two light sources and the endoscope.

10. The system according to claim 8 further comprising a housing in which the at least two light sources and the combiner are at least partially contained.

11. The system according to claim 8 further comprising a collimator coupled to each of the at least two light sources for directing light to the combiner.

12. A method of illuminating a surgical field comprising:
providing at least two light sources selectively actuated to emit light, and a combiner including a scrambler in optical communication with the at least two light sources to receive at least a portion of the light emitted from the at least two light sources and output substantially-uniform combined light with substantially-uniform intensity and color distribution, and
directing light created by the at least two light sources through an endoscope into the surgical field.

13. A method of illuminating a surgical field comprising:
providing at least two light sources selectively emitting light,
combining and scrambling the light from the at least two light sources to provide combined light with substantially-uniform light intensity and color distribution,
directing the combined light with substantially-uniform light intensity and color distribution into the surgical field, and
viewing the surgical field through an endoscope.

14. A method of illuminating a surgical field comprising:
providing at least two light sources selectively emitting light,
combining and scrambling the light from the at least two light sources to provide combined light with substantially-uniform light intensity and color distribution,
directing the combined light with substantially-uniform light intensity and color distribution into the surgical field, and
transmitting the combined light with substantially-uniform light intensity and color distribution through an optical cable that is coupled to an endoscope.

15. A method of illuminating a surgical field comprising:
providing at least two light sources selectively emitting light,
combining and scrambling the light from the at least two light sources to provide combined light with substantially-uniform light intensity and color distribution,
directing the combined light with substantially-uniform light intensity and color distribution into the surgical field, and
directing the combined light with substantially-uniform light intensity and color distribution from a headset.

* * * * *